United States Patent
Vogtherr et al.

(10) Patent No.: US 10,433,823 B2
(45) Date of Patent: Oct. 8, 2019

(54) CONTROL FOR RELIABLE ASSEMBLY AND DISASSEMBLY OF TWO FUNCTIONAL UNITS OF A MULTI-PART MEDICAL DEVICE

(71) Applicant: Aesculap AG, Tuttlingen (DE)

(72) Inventors: Robert Vogtherr, Tuttlingen (DE); Thomas Maser, Zimmern ob Rottweil (DE); Heiko Reichle, Tuttlingen (DE); Dominik Seyfried, Königsfeld (DE); Anton Keller, Dürbheim (DE)

(73) Assignee: Aesculap AG (DE)

( * ) Notice: Subject to any disclaimer, the term of this patent is extended or adjusted under 35 U.S.C. 154(b) by 422 days.

(21) Appl. No.: 15/127,192

(22) PCT Filed: Mar. 17, 2015

(86) PCT No.: PCT/EP2015/055582
§ 371 (c)(1),
(2) Date: Sep. 19, 2016

(87) PCT Pub. No.: WO2015/144501
PCT Pub. Date: Oct. 1, 2015

(65) Prior Publication Data
US 2017/0245844 A1  Aug. 31, 2017

(30) Foreign Application Priority Data
Mar. 26, 2014 (DE) .......... 10 2014 104 179

(51) Int. Cl.
*A61B 17/00* (2006.01)
*A61B 17/02* (2006.01)
*A61B 90/00* (2016.01)

(52) U.S. Cl.
CPC .............. *A61B 17/00* (2013.01); *A61B 17/02* (2013.01); *A61B 2017/00017* (2013.01);
(Continued)

(58) Field of Classification Search
CPC ............ A61B 17/00; A61B 2090/0811; A61B 17/1615; A61B 2090/0808
See application file for complete search history.

(56) References Cited

U.S. PATENT DOCUMENTS

| 4,217,019 A | 8/1980 | Cameron |
| 2007/0049822 A1 | 3/2007 | Bunce et al. |
(Continued)

FOREIGN PATENT DOCUMENTS

| DE | 202004015643 | 12/2004 |
| DE | 102006001677 | 1/2008 |
(Continued)

OTHER PUBLICATIONS

Chinese Office Action for Chinese Application No. 201580020807.4, dated Aug. 24, 2018, with English translaton—11 pages.
(Continued)

*Primary Examiner* — Andrew Yang
(74) *Attorney, Agent, or Firm* — RatnerPrestia

(57) ABSTRACT

A medical device includes two device units having two functional units that can be coupled to each other to actuate the second functional unit via the first functional unit. The first functional unit has a mechanical coupling segment which can be brought into a coupling position to couple with the second functional unit. A detector for detecting a relative position of the two device units or a distance between the two device units is provided on at least one device unit. The electrical or electronic control of the first functional unit is configured such that the mechanical coupling segment of the first functional unit can be brought into the coupling position only if the two device units are in a certain position with respect to each other or fall below a minimum distance from each other.

14 Claims, 8 Drawing Sheets

(52) U.S. Cl.
CPC .............. *A61B 2017/00039* (2013.01); *A61B 2017/0046* (2013.01); *A61B 2017/00314* (2013.01); *A61B 2017/00477* (2013.01); *A61B 2017/00539* (2013.01); *A61B 2017/00544* (2013.01); *A61B 2017/0243* (2013.01); *A61B 2090/0808* (2016.02); *A61B 2090/0811* (2016.02)

(56) References Cited

U.S. PATENT DOCUMENTS

| | | |
|---|---|---|
| 2007/0179477 A1 | 8/2007 | Danger |
| 2012/0157788 A1 | 6/2012 | Serowski |
| 2013/0060278 A1* | 3/2013 | Bozung ............ A61B 17/32002 606/205 |
| 2013/0324998 A1 | 12/2013 | Kimball et al. |

FOREIGN PATENT DOCUMENTS

| | | |
|---|---|---|
| DE | 102006033439 | 1/2008 |
| JP | 2009000426 | 1/2009 |
| WO | 9716123 | 5/1997 |
| WO | 2007027470 | 3/2007 |
| WO | 2013181100 | 12/2013 |

OTHER PUBLICATIONS

International Search Report and Written Opinion of the International Searching Authority for International Application No. PCT/EP2015/055582, dated Aug. 14, 2015, 7 pages.
German Search Report dated Jan. 27, 2015 for German Application No. 10 2014 104 179.8, including translation, 12 pages.
European Office Action dated Jul. 6, 2016 for European Application No. 15710195.7, including translation, 6 pages.

* cited by examiner

| S1 | S2 | S3 | Q |
|---|---|---|---|
| 0 | 0 | 0 | 0 |
| 1 | 0 | 0 | 0 |
| 0 | 1 | 0 | 0 |
| 1 | 1 | 0 | 0 |
| 0 | 0 | 1 | 1 |
| 1 | 0 | 1 | 1 |
| 0 | 1 | 1 | 0 |
| 1 | 1 | 1 | 1 |

CONTROL FOR RELIABLE ASSEMBLY AND DISASSEMBLY OF TWO FUNCTIONAL UNITS OF A MULTI-PART MEDICAL DEVICE

RELATED APPLICATIONS

This application is the United States National Phase of International Application No. PCT/EP2015/055582, filed Mar. 17, 2015, which claims the benefit of priority of German Application No. 10 2014 104 179.8, filed Mar. 26, 2014. The contents of International Application No. PCT/EP2015/055582 and German Application No. 10 2014 104 179.8 are incorporated by reference herein in their entireties.

FIELD

The present invention relates to a multi-piece medical device comprising two device units which can be mechanically coupled to each other and two functional units which can be mechanically coupled to each other as well as to a corresponding method. Specifically, the present invention relates to a generic medical device comprising a first functional unit and a second functional unit, wherein in the mechanically coupled state the second functional unit can be operated by power with the first functional unit, the first functional unit being able to be electrically or electronically actuated and comprising a mechanical coupling segment which can be brought into a coupling position in order to couple with a corresponding mechanical coupling segment of the second functional unit.

BACKGROUND

In many surgical interventions, power-operated devices are used in modern days, which are able to perform or control specific works or movements. To mention an example, there is a surgical device for stabilizing or immobilizing a part of a moved tissue or also for the positioning of organs or surgical instruments and devices during an operation by means of a movable holding arm. Such a movable holding arm can be brought from its locked state into a movable state by means of compressed air. The control of the compressed air is achieved here by means of an electronic control system, which is supplied with the signals from actuation elements and sensors.

Furthermore, various instruments and devices have a two-part design, since on the one hand, one part of the device cannot be conditioned and sterilized due to the geometry, the employed materials or the like or is subject to such a high wear and tear that it is provided for single use only; or on the other hand, a further part of the device comprises components which are so expensive that a single use is not reasonable from the economic point of view.

The combination of this two-part design with a power-operated device or a device which is controlled by or operated with external energy results in various technical problems, which in turn result from the assembly and disassembly or the connection of the control or working equipment of both parts of the device.

In the mentioned example, it is necessary to connect two parts to each other, namely a technical unit enabling the power-operated locking of the movable holding arm, and the holding arm itself. Both parts of the device comprise an actuation element each, by means of which a slider can be moved in the technical unit. The actuation elements have the same function. Upon operating one of these actuation elements in the adapted state of the holding arm, the slider moves forward out of the housing against a compression spring. If the actuation elements are not operated, however, the slider is pressed rearward into the housing of the technical unit by spring force. Both actuation elements are implemented as a pushbutton. This is why the surgeon during use does not have to switch over between activating and deactivating the working procedure. The return of the slider and hence the locking of the holding arm occurs automatically by the spring force of the compression spring as soon as the actuation element is released.

The actuation elements are also required for assembling and disassembling the two parts: The actuation element provided on the technical unit makes the slider move forward, and then the holding arm can be adapted. If the actuation element is let go, the holding arm will be locked first. Subsequently, it is possible to work with the entire device and the two actuation elements. For disassembly, the actuation element of the technical unit is activated again, the slider is moved and the holding arm can be detached from the technical unit.

On the one hand, these procedures are not comfortable. As the actuation element is implemented as a pushbutton, it must not be released during the assembly or disassembly phase. If the electrical signal of the actuation element is interrupted, for instance due to the user performing a short unconscious movement during the assembly or disassembly phase, the slider immediately retracts into the housing of the technical unit. If the connection of the holding arm is not correctly adapted in the slider at that moment, it may happen that components of the technical unit or of the holding arm are damaged due to the return motion. If the user needed both hands for a short time during the assembly or disassembly phase, because something got jammed and the adaptation process is sluggish, this would not be possible for him as he must not let go of the actuation element.

On the other hand, the assembly and disassembly phases involve a considerable risk for the user. As long as he keeps the actuation element on the technical unit in the activated position with one hand, the slider is extended and is not covered any more by the housing. The slider has a geometry which is open toward the top, so that the adapting of the connection of the holding arm is made possible. A lateral insertion or other solutions for reducing the risk of this geometry seem to be impractical. By way of example, it may happen that the user puts his finger into said open geometry of the slider, if he discovers for instance some dirt in said adaptation site and wants to remove it. If he now released the actuation element, the slider would abruptly retract into the housing of the technical unit by means of the spring force. This may pose a high risk of injury for the user.

A technically comparable system is represented by the pneumatic bone punch according to DE 20 2004 015 643 U1. This device works pneumatically and consists of the handle piece comprising all technical devices which allow a power-operated functioning, and a punch shaft which has to be placed in the handle piece or adapted with it. With this system, a safety lever and an ON/OFF-switch are promoted which both reduce the risk of accidents resulting from such a power-operated system. The safety lever blocks the mechanism of the punch during cleaning the punch shaft, in other words if the user has to reach into the working area of the punch on purpose. This blocking is achieved in a purely mechanical fashion.

The ON/OFF switch is actually a pushbutton switch in the technical sense, activating the device in the pressed state and upon releasing the pushbutton automatically changing to the state "OFF" or "device inactive". The ON/OFF switch additionally comprises a rotary switch which is installed so as to be hidden. By means of this additional switch, the main switch or main pushbutton can be blocked in order to prevent an unintentional operation of the device, for instance during placing it on an uneven underground, whereby the on-switch could be activated by the own weight of the device. This blocking is achieved in a mechanical manner, too.

The solutions which are supposed to allow safe working with the bone punch according to DE 20 2004 015 643 U1 need a sufficient installation space. The safety lever which has to absorb and withstand the full punching force and is constructed with a sufficient safety factor, cannot always be implemented in certain devices which likewise operate with high forces but have a substantially higher compactness. The larger disadvantage is, however, that this mechanism is not automatically in effect and may be forgotten.

SUMMARY

Therefore, the present invention is based on the object to provide a multi-piece medical device and a corresponding method which allows a user in a simple manner to comfortably and safely assemble and disassemble two functional units of two device units which are to be coupled to each other.

According to the invention, an electronic circuit concept or control method is proposed for a two-part medical device, in particular surgical device, which works on a power-operated basis and is electronically controlled, with the control concept minimizing the risks of the device which exist in particular prior to or during the adaptation of the second device unit. Further, the control concept allows a comfortable assembly or adaptation of the two devices to each other.

A multi-piece medical device according to the invention comprises two device units that can be mechanically coupled to each other, wherein the two device units have two functional units that can be mechanically coupled to each other in order to be able to actuate (by power) the second functional unit by means of the first functional unit in the mechanically coupled state. Here, the first functional unit can be controlled electrically or electronically and has a mechanical coupling segment which can be brought into a coupling position in order to couple with a corresponding mechanical coupling segment of the second functional unit. According to the invention, means for detecting a relative position of the two device units with respect to each other or a distance of the two device units from each other are provided at least on one device unit, and the electrical or electronic control of the first functional unit is configured in such a way that it can be brought into the coupling position only if the two device units are in a certain relative position with respect to each other or fall below a predetermined minimum distance from each other.

This configuration or switching logic of the device minimizes the risks for the operator occurring during mounting or dismounting the two device parts. The activation proceeds in dependency on distance and hence works automatically; what is more, it cannot be forgotten or overlooked in contrast to many conceivable mechanical solutions.

Due to the simplicity of the assembly and disassembly, this is also more user-friendly. For the distance-dependent electrical or electronic activation of the first functional unit, electrical components may be used which only have a low space requirement as compared to mechanical safety means.

This space is actually often not available with medical devices. On the other hand, the device comprising such a circuit can be realized so as to have a substantially more compact design than with a comparable mechanical solution.

The relative position or the minimum distance can be selected such that a user cannot put his hand or finger between both device units or the two device units cover the two coupling segments of the functional units in such a way that a user cannot reach them with his hand or finger.

This allows to ensure—even with a careless handling of the medical device—that the user cannot reach into the coupling segment which has been brought into the extended or coupling position and the fingers cannot be squeezed or injured in any other way during the retraction of the coupling segment.

According to one configuration, the minimum distance can be equal to or smaller than 40 mm, in particular equal to or smaller than 20 mm, particularly preferred equal to or smaller than 15 mm.

The means for detecting a relative position or a distance between the two device units may be realized in particular as a magnetic proximity switch or proximity sensor provided on or at least near the coupling segment of the first functional unit, said switch or proximity sensor being able to be triggered by appliances, in particular by magnets which are provided on or at least near the coupling segment of the second functional unit, said triggering being effected if the first coupling segment is brought near the second coupling segment while falling below the minimum distance. As an alternative, it is possible to use an independent distance sensor which is provided on a device unit and is capable of measuring the distance between the two device units without any further means on the other device unit.

The proximity switch or proximity sensor is first triggered, activated or switched upon reaching the predetermined relative position or falling below the predetermined minimum distance of the device units and/or functional units, and stays in this state until the device units or functional units leave the predetermined relative position again or have the minimum distance or exceed it, e.g. during the disassembly of the two device units.

This allows a contact-less and automatic activation of the proximity sensor or proximity switch and hence an associated control of the first functional unit without further action on part of the operator.

The proximity switch or distance sensor may be installed in the device unit of the first functional unit so as to be flush-mounted or concealed. Depending on the strength of the magnet and the sensibility of the proximity switch, a certain material thickness of the housing of the technical block may be present between the two parts.

This results in a minor hazard of soiling or damaging the proximity sensor or proximity switch. Further, it is not immediately subjected to the influences during the preparation by sterilization.

According to an additional or alternative aspect, the two functional units may be simultaneously coupled during the coupling of the device units.

This has the advantage that both the two device units and the two related functional units are coupled to each other in the course of one motion or one procedure. During coupling of the device units, the functional units are automatically brought into a predetermined coupling position.

If the device units have been being mechanically coupled to each other, they may also be in the electrically coupled state and/or coupled in terms of signal transfer.

This means that upon coupling the device units, the latter are not only mechanically connected but also electrically connected and/or connected in terms of signal transfer, in order to be able to actuate the second device unit or any other functional units provided there, but also to be able to act on the first device unit and functional unit or actuate it via the second device unit, e.g. by corresponding control means or actuation elements provided there.

The mechanical and electrical and/or the signal-related interfaces between the two device units may be configured such that during coupling the two device units, the electrical and/or signal-related coupling is not effected until the mechanical coupling is completed, and during decoupling the two device units, the electrical and/or signal-related coupling is released before the mechanical coupling.

By this measure, it is achieved that the complete mechanical coupling or releasing of the same is detected and a corresponding activation of the functional units or of the mechanical coupling segment of the first functional unit may be effected. This is why the electrical and/or signal-related coupling may be accompanied by an automatic return of the coupling segment to a predetermined position, e.g. resting position, and/or during releasing the electrical and/or signal-related coupling of the coupling segment it can be automatically brought or extended into the coupling/decoupling position. During decoupling, the coupling segment may further be kept in the coupling position until the minimum distance between the two device units is exceeded, and after exceeding the minimum distance it can be automatically brought into the predetermined position.

Thus, the user is not bothered with a specific sequence of actuation processes to be carried out for the assembly and disassembly of the device units and functional units.

The coupling segment of the first functional unit can be spring-biased into a predetermined position and can be brought into the coupling position by means of external power, in particular by hydraulic or pneumatic pressure or by means of an electric motor.

This allows to simplify the activation of the functional units by merely having to actively electrically control the moving or actuation direction in one direction, the moving or actuation direction in the other direction being effected by a mechanical return. This allows to simplify the electrical operation as a whole. As an alternative, it is also possible to actively control the functional units in both moving or actuation directions (by hydraulic, pneumatic or electromotive ways and means).

In the coupled state of the two device units, the first functional unit and indirectly the second functional unit by actuating a first actuation element provided on the first device unit, can be electrically or electronically actuated, and in the decoupled state of the two device units, the coupling segment of the first functional unit can be automatically brought into the coupling position by means of the external power, if the two device units are in the specific relative position with respect to each other or have fallen below the predetermined minimum distance with respect to each other.

Thus, solely one actuation element allows to control both the normal operation of the functional units and the coupling and decoupling processes. This makes it possible to avoid the provision of additional actuation elements and corresponding connection lines merely for the coupling and decoupling of the device units and functional units, and possibly related maloperations by the user.

According to an additional or alternative aspect, in the coupled state of the two device units, the first functional unit and indirectly the second functional unit can be electrically or electronically actuated by operating a second actuation element provided on the second functional unit, and the second actuation element may be configured in particular as an electrical break contact and such that the supply of energy for the activation of the first functional unit, for instance the supply of energy for the activation of the first functional unit, is interrupted during the electrical coupling of the two device units.

This configuration has two advantages. On the one hand, the first functional unit and indirectly the second functional unit may also be actuated through an actuation element on the second device unit. At the same time, the circuit-related linkage of the second actuation element in the overall circuitry may be implemented such that the adaptation or electrical coupling of the second device unit results in a predetermined electrical control in the first device unit.

According to an additional or alternative aspect, the coupling segment can be brought into a predetermined working position in the coupled state by operating the first or the second actuation element. This predetermined working position may correspond to the coupling position or decoupling position.

This allows to minimize the number of possible working positions and hence the activation of the functional units, more precisely of the first functional unit, in which case the circuit concept can have an even simpler design.

According to an aspect of the invention, the first device unit may be a technical unit which is connected to an electrical external power source, and the second device unit may be a flexible segmented arm which can be connected to the technical unit and be brought into different positions and/or locations. The first functional unit may be a tensing mechanism and the second functional unit may be a traction cable, capable of being coupled to the tensing mechanism, which is passed through the articulated elements of the segmented arm and allows to brace the articulated elements against one another in a friction-type connection, in order to make the segmented arm lockable in a desired location.

This is why the adaptation/circuit concept according to the invention can be applied to a surgical device for stabilizing or immobilizing of moving organs.

A further aspect of the present invention relates to a method of mechanically coupling two functional units of a two-piece or multi-piece medical device, wherein the medical device comprises two device units that can be mechanically coupled to each other, the two device units have two functional units that can be mechanically coupled to each other in order to be able to actuate (by power) the second functional unit by means of the first functional unit in the mechanically coupled state, and the first functional unit can be controlled electrically or electronically and has a mechanical coupling segment which can be brought into a coupling position in order to couple with a corresponding mechanical coupling segment of the second functional unit. According to the invention, the method comprises the following steps: detecting a relative position or a distance of the two device units relative to each other; and configuring the electrical or electronic control of the first functional unit in such a manner that the mechanical coupling segment of the first functional unit is brought into the coupling position only if the two device units are in a specific relative position with respect to each other or fall below a predetermined minimum distance with respect to each other.

The method according to the invention has the same advantages as described in the context with the medical device according to the invention.

BRIEF DESCRIPTION OF THE DRAWING FIGURES

FIG. 9 shows a logical diagram according to the preferred embodiment of the invention.

DETAILED DESCRIPTION

Figure 1:
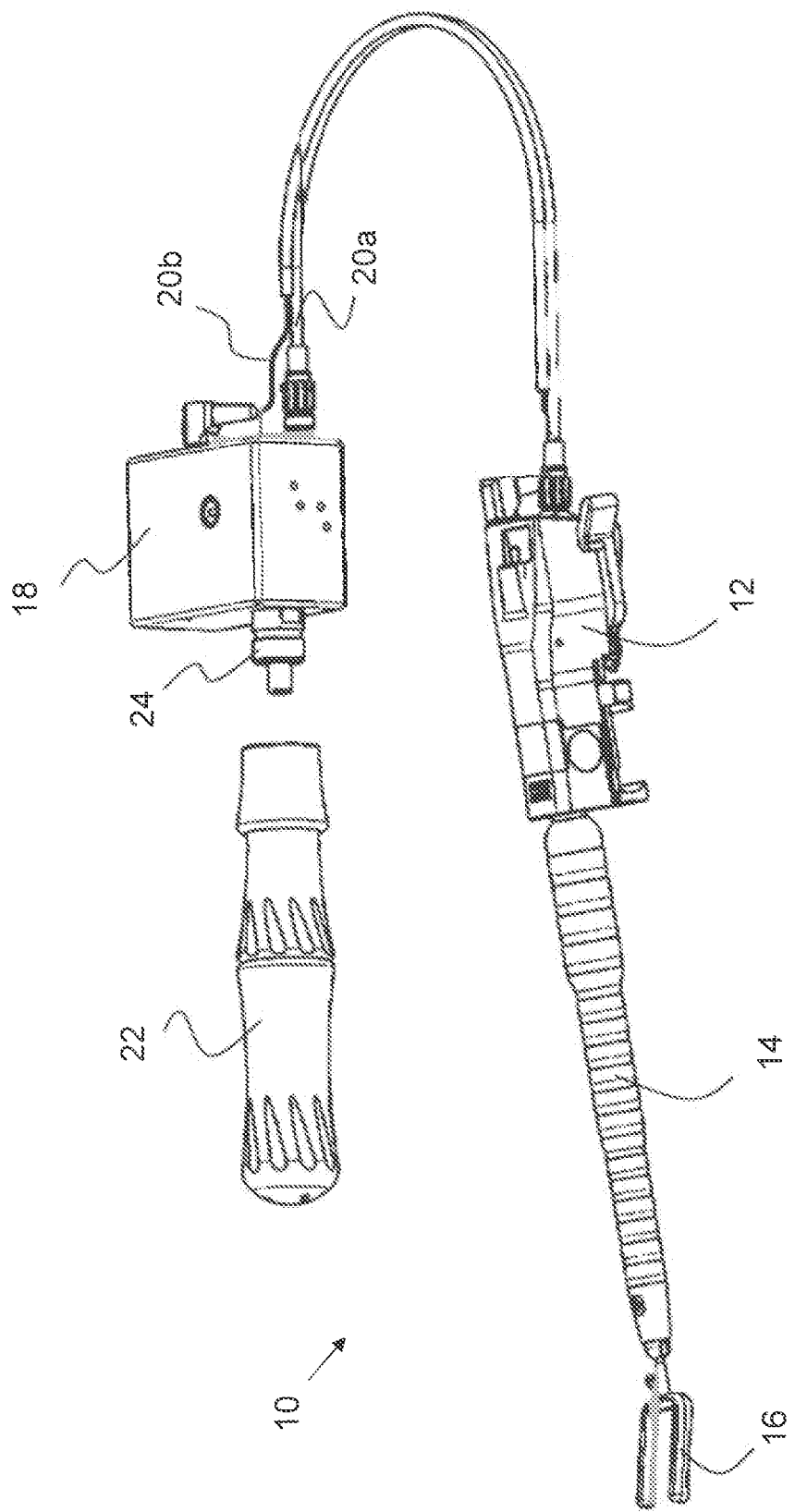
FIG. 1 shows a perspective view of a surgical device according to a preferred embodiment of the invention.

FIG. 1 shows a perspective view of a multi-piece medical device in the form a surgical device 10 for stabilizing or immobilizing a zone of moved tissue or also for the positioning of organs, according to a first embodiment of the invention. The device 10 comprises a base body or technical block 12 to which a movable holding arm, more precisely a flexible segmented arm 14, is attached, whose free end is provided with a holding element 16 for holding the tissue or organ. The device 10 further comprises an adaptation unit 18 which is in connection with the technical block 12 via several lines 20. A compressed air cartridge 22, serving as an external source of energy and supplying the working medium which is necessary for actuating the tensing mechanism for the segmented arm 14 integrated in the technical block 12, can be connected to a compressed air connection 24 on the adaptation unit 18. Compressed air is conveyed from the adaptation unit 18 through a compressed air line 20a to the technical block 12. A signal line 20b extending parallel thereto serves for controlling the fluid control elements or valves (not shown) which are provided in the adaptation unit 18 and are able to be actuated by the technical block 12 or segmented arm 14.

Figure 2:
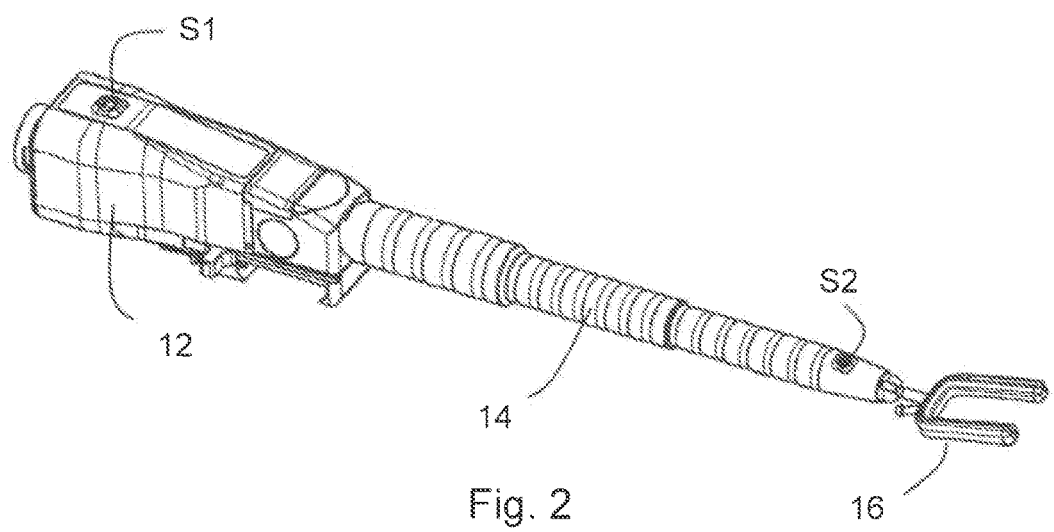
FIG. 2 shows a technical block including a coupled segmented arm of the surgical device shown in FIG. 1.

FIG. 2 only shows the technical block 12, the segmented arm 14 and the holding element 16 in an enlarged representation. The technical block 12 essentially comprises the entire technical system for tensing the segmented arm 14 as well as for fixing the whole system to external supports (not shown) such as e.g. a sternum spreader. Here, the technical block 12 constitutes a reusable technical module A and the segmented arm 14 together with the holding element 16 constitutes a working module B (see FIG. 3) designed for single use. By way of example, the technical modules A and B represent two device units in the sense of the claims and can be coupled to each other.

It can also be seen in FIG. 2 that the technical block 12 is provided with a first actuation element S1 in the form of an electrical pushbutton or switch, and the distal end of the segmented arm 14 is provided with a second actuation element S2, likewise in the form of an electrical pushbutton or switch. Both actuation elements S1 and S2 serve for controlling the flow of energy from the external source of energy, i.e. for controlling the compressed air which is conveyed from the compressed air cartridge 22 via the compressed air line 20a and a compressed air connection 26 to the technical block 12. The actuation elements S1, S2 and the activation scheme of the external source of energy is configured such that in the coupled state of said two device units the flow of energy is enabled as long as the actuation elements S1, S2 are pressed or operated.

Figure 3:
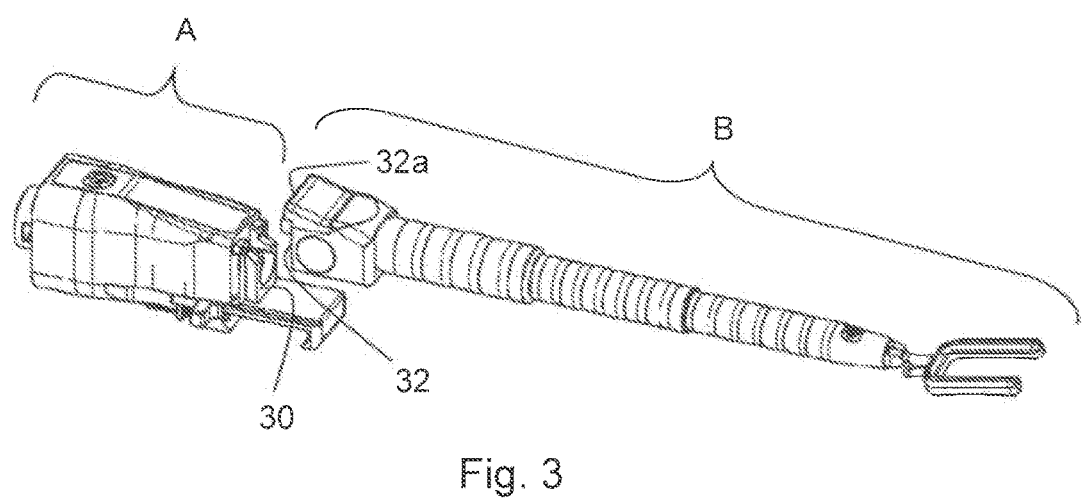
FIG. 3 shows a technical block with a decoupled segmented arm of the surgical device shown in FIG. 1.

FIG. 3 shows the modules A and B separated from each other and also the associated coupling segments 30 and 32 of the two modules A and B.

Figure 4:
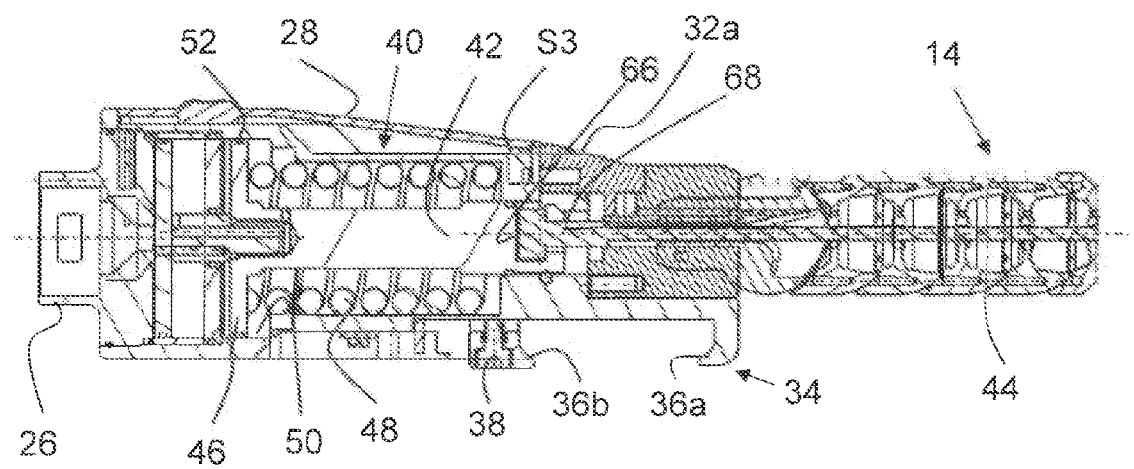
FIG. 4 shows a cross-sectional view of the technical block shown in FIG. 2.

FIG. 4 shows a cross-sectional view of the technical block 12 and of a part of the segmented arm 14 coupled thereto. In addition to the coupling segment 30 for coupling the working module B, the technical block 12 comprises a housing portion 28 and a fastening portion 34 for attaching the technical block 12 to a (not shown) support such as a sternum spreader. The housing portion 28 may be provided with ergonomically recessed grips, so that the assembly and disassembly of the working module B can be simplified.

The fastening portion 34 comprises two undercut clamping jaws 36a and 36b which can be adjusted in width with respect to each other and with which the technical block 12 can be fastened to a corresponding rail or similar supporting device in a frictional-fitting and form-locking manner. One of the two clamping jaws 36b is adjustable and can also be fixed by means of a clamping screw 38.

The housing portion 28 accommodates a mechanical piston/cylinder system 40 representing an essential component of the tensing mechanism. A slider or carriage 42 which is guided in the housing portion 28 in the axial direction (i.e. in the longitudinal direction of the segmented arm 14) and can be connected to a traction cable 44 guided in the segmented arm 14, is connected to an end of a piston 46 of the mechanical piston/cylinder system 40, so that a lifting movement of the piston 46 results in a translational, axial shifting of the carriage 42.

The piston 46 is biased by means of a spiral compression spring 48 into a direction in which the piston 46 pulls the traction cable 44 toward the technical block 12 via the carriage 42 and in this way tensions the segmented arm 14 and its articulated elements and immobilizes and stiffens it/them. Due to the spring preload, the segmented arm 14 when in the state of rest, i.e. without any external intervention, is in the immobilized or locked condition.

In order to be able to bend the (per se) flexible segmented arm 14 in any direction, the spring preload has to be neutralized. This is achieved by means of an external source of energy. The piston 46 can be operated with the aid of compressed air, which is supplied to a cylinder chamber 50 of the mechanical piston/cylinder system 40 via the compressed air connection 26, against the compression force of the spiral compression spring 48 in the opposite direction and, in this process, can release or slacken the traction cable 44 by a corresponding shifting of the carriage 42 and thus loosen the immobilized segmented arm.

One or more piston rings 52 serve for the fluid-tight separation between the part of the cylinder chamber 50 which is acted upon with compressed air and the part of the cylinder chamber 50 in which the spiral compression spring 48 is disposed. The movement of piston 46 and carriage 42 respectively is limited in both directions by a stop, in order to preset defined adjustment distances for releasing and tensing in each case.

The process of coupling the working module B to the technical module A will be described in more detail below.

The interface between the working module B and the technical module B does not only serve for the pure mechanical coupling of said two units, but also for the signal-related and functional coupling, as on the one hand the control signals input via the distal actuation element S2 have to be transmitted to the technical block 12 and from there via the control signal line 20b to the adaptation unit 18 with the corresponding control organs and, on the other hand, the traction cable 44 extending in the segmented arm 14 has to be coupled to the mechanical piston/cylinder system 40.

Figure 5:
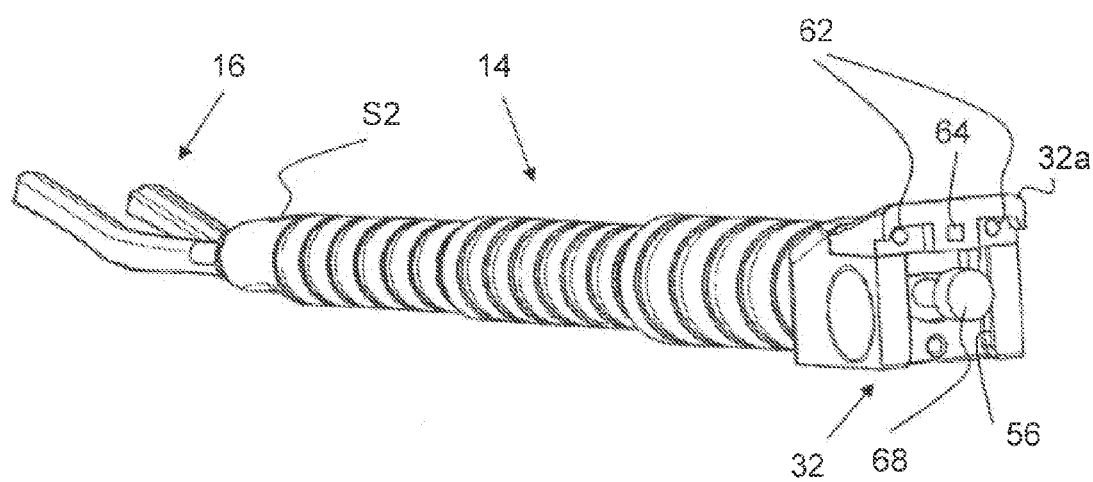
FIG. 5 shows a perspective view of the segmented arm.

For mechanically coupling the module A to the module B, the coupling segment 30 of the technical block 12, which is immediately above the fastening portion 34, comprises a vertically extending dovetail guide 54 which constitutes a form-locking connection with a complementarily shaped guide seat 56 on a coupling segment 32 of the working module B (see FIG. 5). To this end, the coupling segment 32 is vertically pushed onto the dovetail guide 54 until the two coupling segments 30 and 32 come into a full-surface contact. For detachably locking the two coupling segments 30 and 32, the coupling segment 32 of the working module B is provided with a locking element 58 in the form of a spring-biased locking nib.

The coupling segment 32 of the working module B further comprises a protruding portion 32a projecting toward the technical module A and covering the coupling segment 30 of the technical module A from above, i.e. in inserting direction, during the coupling of the two modules A and B, so that it is hardly possible to put the hand or the fingers between the two coupling segments 30 and 32 from above.

In addition, the front side of the coupling segment 32, more precisely the protruding portion 32a, is provided with two electrical contacts 62 which come into contact with corresponding contact points 60 on the coupling segment 30 of the technical block 12 when the two modules A and B are in their coupled and locked working position. The electrical contacts 62 are in connection with the distal actuation element S2 via (not illustrated) electrical lines.

The interior of the technical block 12 also accommodates (not illustrated) lines which connect the contact points 60 to the outgoing control line 20b.

Further, a switching element in particular in the form of a proximity switch S3 which can be activated in a contactless manner is provided or installed on the coupling segment 30 of the technical block 12. In the described exemplary embodiment, the switch is a magnetic proximity switch such as a Reed relay or a Hall sensor, for instance, which can be triggered by a small magnet 64 in the proximal end or coupling segment 32 of the segmented arm 14. The proximity switch S3 may be flush-mounted in the technical block 12 or installed so as to be concealed in order to minimize the risk of being soiled or damaged and reduce the influences during the preparation by sterilization. Depending on the strength of the magnet 64 and the sensibility of the proximity switch S3, a certain material thickness (of a magnetically non-conducting material) of the housing 28 of the technical block 12 may be present between the two parts. By a corresponding selection and adjustment of the proximity switch S3 and of the magnet 64, a minimum distance between the technical block 12 and the segmented arm 14 can be correspondingly set as from which the proximity switch S3 will be triggered.

Further, an end piece 68 of the traction cable 44 can be seen in FIG. 5. The end piece 68 is a rotationally symmetrical profiled turned part which fits exactly in a corresponding recess 66 in the carriage 42 and in this way can be connected to the carriage 42 in the axial direction or tensile direction in a form-locking manner. The end piece 68 on the free end of the traction cable 44 further ensures that the traction cable 44 guided by the coupling segment 32 does not get thread out.

By way of example, the recess 66 in the carriage 42 represents a (first) coupling segment of the first functional unit, i.e. of the part of the tensing mechanism provided in the technical block A, and the end piece 68 of the traction cable 44 represents a (second) coupling segment of the (second) functional unit, i.e. of the part of the tensing mechanism provided in the working module B.

Both the proximity switch S3 and the magnet 64 are in close proximity of the segments of the two functional units to be coupled, i.e. close to the recess 66 in the carriage 42, on the one hand, and close to the end piece 68 of the traction cable 44 on the other hand.

Figure 6A:
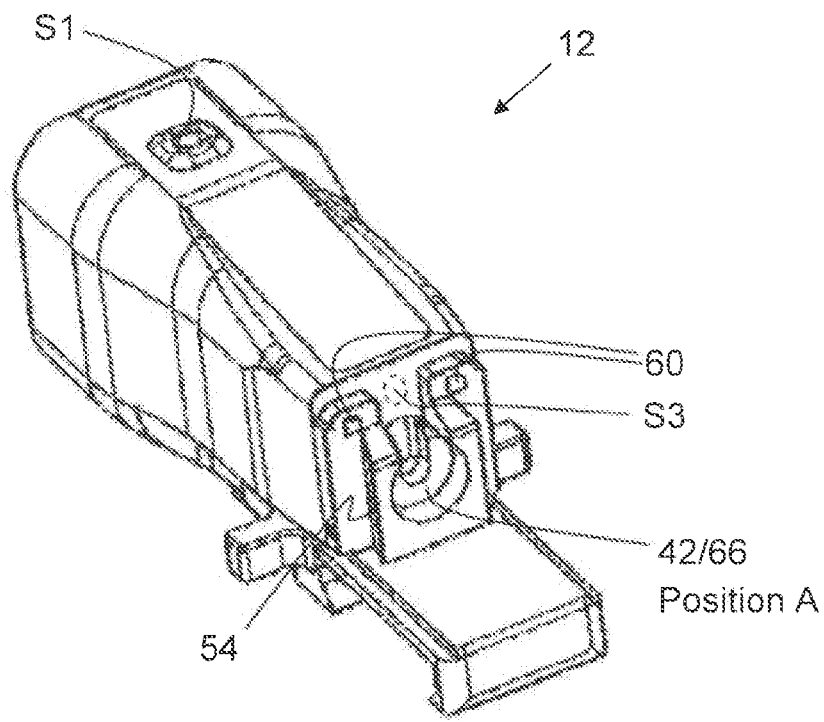
FIG. 6A shows a perspective view of the technical block including a carriage of a tensing mechanism in its resting position.
Figure 6B:
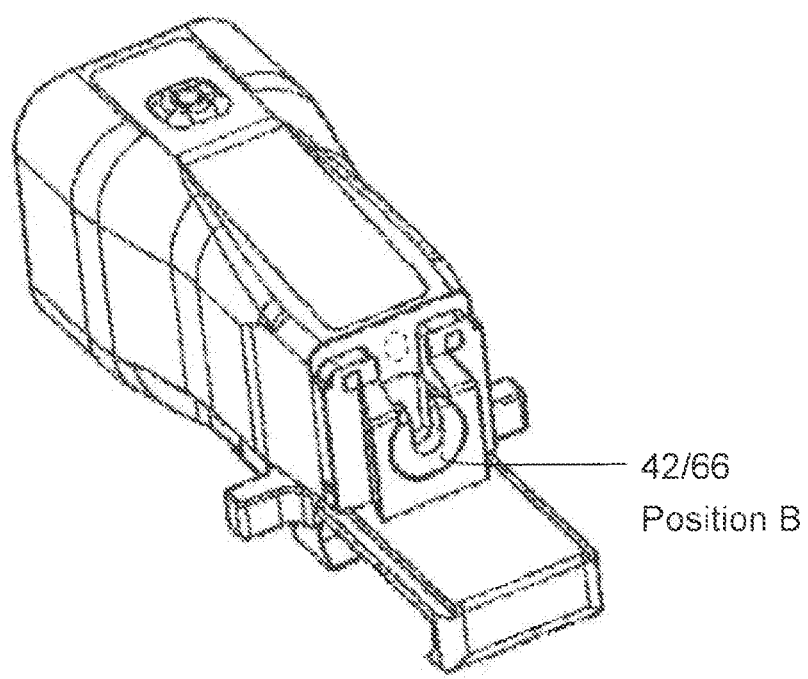
FIG. 6B shows a perspective view of the technical block including the carriage of the tensing mechanism in its coupling position.

FIG. 6A shows a perspective view of the technical block including the carriage 42 in its retracted resting position (position A) and FIG. 6B shows a perspective view of the technical block including the carriage 42 in its extended coupling position (position B). In the retracted resting position (position A), the carriage 42 together with the recess 66 is retracted in the housing 28 to such an extent that the end piece 68 of the traction cable 44 cannot be inserted. In this position, the carriage 42 does not pose a danger for the user.

In the following, the process of coupling the carriage 42 (first functional unit) to the traction cable 44 (second functional unit) is described in detail:

The end piece 68 of the traction cable 44 can be inserted in the recess 66 from above if the carriage 42 is in the fully extended position or coupling position. As the carriage 42 is retracted in the state of rest due to the preload of the spring 48, the carriage 42 has to be extended by means of the mechanical piston/cylinder system 40 in order to insert the end piece 68 in the recess 66.

As long as the carriage 42 extends out of the housing (coupling position B) and the segmented arm 14 is not adapted yet, the open recess 66 in the carriage 42 in connection with the strong spring force of the spring 48 represents a considerable source of danger for the user.

If, as described above, a magnet 64 in the proximal end of the segmented arm 14 is sufficiently close to the proximity switch S3 of the technical block 12, the circuit enables the extending of the carriage 42. The strength of the magnet 64 and the sensitivity of the proximity switch S3 are here adapted such that the carriage 42 can not extend until the proximal end of the segmented arm 14, more precisely the protruding portion 32a, conceals the recess 66 in the carriage 42 to a sufficient extent, so that it is not possible for the user to put a finger therebetween, for instance.

If the segmented arm 14 is fully adapted, the two coupling segments 30 and 32 have a full-area contact and the electrical contact between the contact points 60 on the technical block and the contacts/mating elements 62 of the segmented arm 14 is closed. In the adapted and non-operated basic state, the contact points 60 and the mating elements 62 are short-circuited by the break contact S2. This makes it possible to distinguish between the states "adaptation process running" and "ready for operation".

In order to close the contact, the pushbutton switch S2 of the holding arm must be an electrical break contact. This signal makes the carriage 42 move back again, the latter straining the traction cable 44 in the segmented arm 14. Now it is possible to normally work with the two actuation elements S1 and S2, and pressing one of the actuation elements S1 or S2 results in releasing the tensing mechanism and hence the locked state of the segmented arm 14, and releasing or not operating the actuation elements S or S2 results in the segmented arm 14 being locked again.

For disassembling the segmented arm 14, the actuation element S1 on the technical unit S1 is pressed and the carriage 42 extends. As soon as the segmented arm 14 is lifted a little bit, the electrical contact between the contact points 60, 62 is opened and the signal which makes the carriage 42 extend is maintained by the circuit.

The user may now release the actuation element S1 and has both hands available for further disassembly. If the connection of the segmented arm 14 is fully extended from the carriage 42 and the segmented arm 14 is removed from the technical unit 12, the signal of the proximity switch S3 is interrupted and the carriage 42 moves back to its resting position again if the magnet 64 has moved away by a corresponding distance (at least by the desired and adjusted minimum distance).

Figure 7:
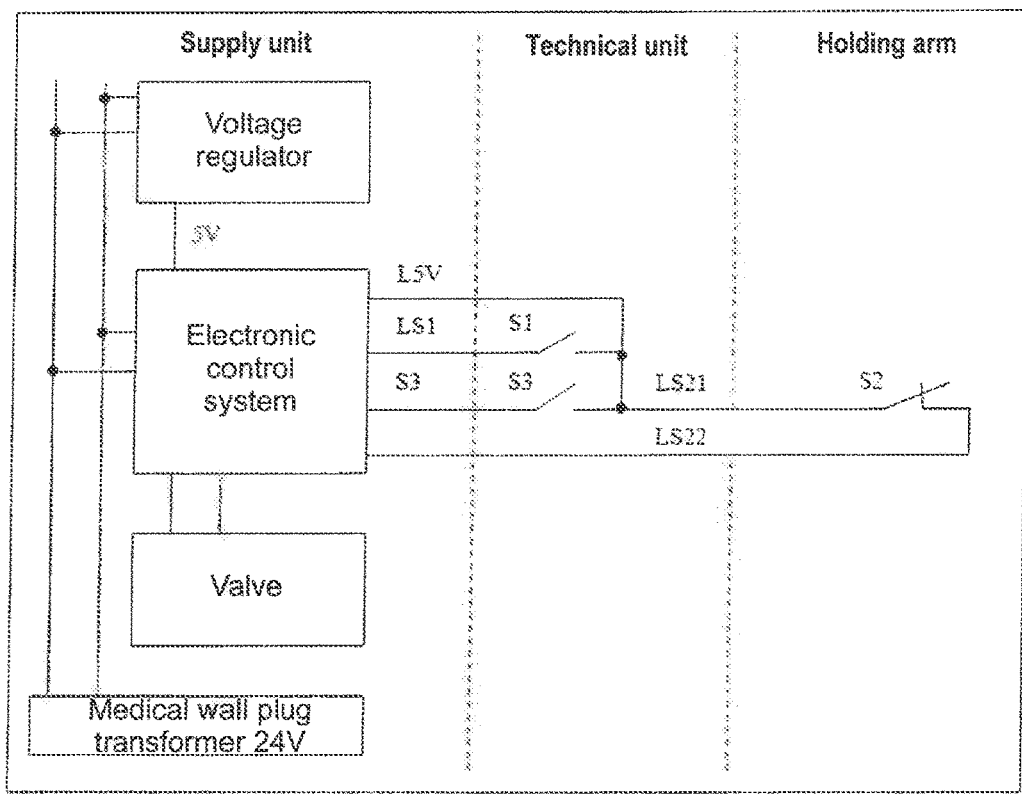
FIG. 7 shows an electrical wiring diagram according to the preferred embodiment of the invention.
Figure 8:
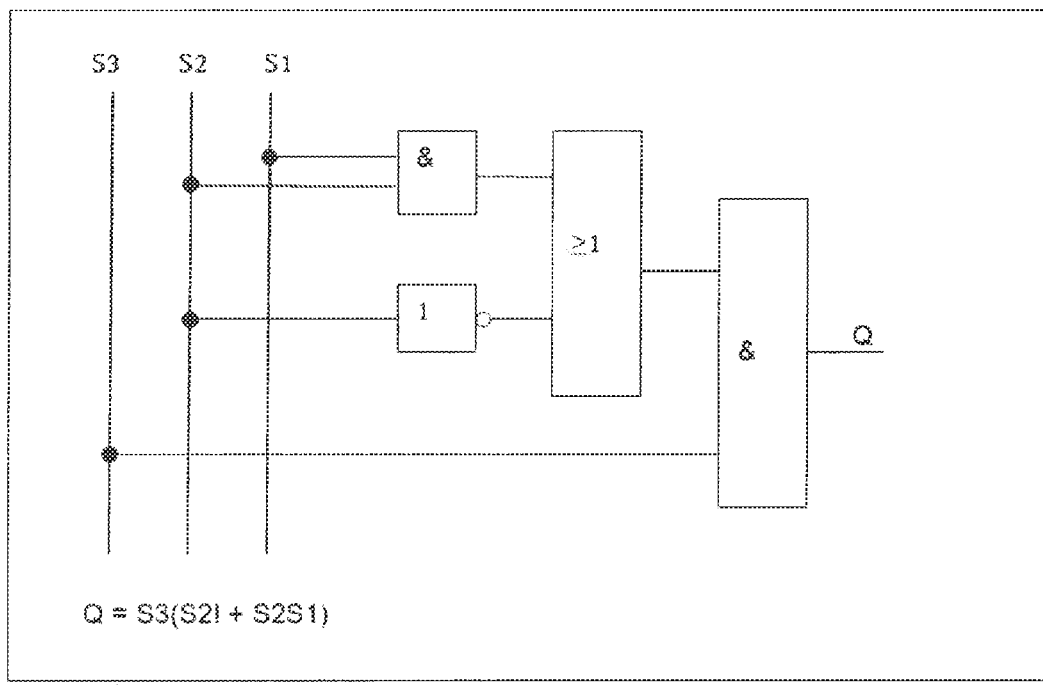
FIG. 8 shows a switching logic according to the preferred embodiment of the invention.

In the following, the functions and switching commands of the actuation elements and switches are explained in detail with reference to FIGS. 7 to 9, with FIG. 7 showing an electrical wiring diagram, FIG. 8 showing a switching logic and FIG. 9 showing a logical table.

In the technical block (first device unit), the actuation element or make contact S1 has the function to release the segmented arm. The proximity switch S3 serves for detecting an adaptation or coupling process of the segmented arm 14. The proximity switch S3 is configured such that it switches at an early point in time during the coupling process, so that the rope end 68 can be hooked into the carriage 42, and switches at a late point in time during the decoupling process, to make sure that the rope end 68 has been completely taken out of the carriage 42.

The actuation element or break contact S2 provided on the segmented arm 14 likewise has the function to release the segmented arm.

For coupling the two functional units made up of carriage 42 and rope 44, the proximity switch S3 is open first. Neither the actuation element S1 nor the actuation element S2 must be operated or in the operated state. If the proximity switch S3 closes due to the approach of the magnet 64 provided on the holding arm 14, the carriage 42 moves out to the coupling position and the rope end 68 can be hooked in. If the two modules A and B are fully coupled, an electrical contact between the contacts 60 and 62, i.e. between both modules A and B, is established and the break contact S2 is closed, whereupon the carriage 42 returns to its resting position again and the medical Instrument 10 is ready for operation.

In the course of decoupling or removing the working module B or segmented arm 14, the proximity switch S3 is closed for the time being and the carriage 42 is operable. If one of the two actuation elements is actuated, i.e. either the make contact S or the break contact S2, the carriage 42 extends. If the segmented arm 14 is detached from the technical block 12, the electrical contact between the contacts 60 and 62 is interrupted and S2 is opened. This has the effect that the carriage 42 remains in its extended position or coupling/decoupling position without having to continue to operate one of the two actuation elements S1 or S2. In this coupling position, the rope end 68 is released and the working module B can be completely removed. As soon as there is a certain distance (minimum distance) between the magnet 64 and the proximity switch S3, the make contact S3 opens and the carriage 42 is retracted into the technical block 12 due to the spring preload.

In the logical table illustrated in FIG. 9, Q represents the position of the carriage 42, with "1" identifying the extended position or coupling position and "0" identifying the retracted position or resting position. If the proximity switch S3 is open, i.e. the distance between the two device units 12, 14 is larger than or equal to the minimum distance, it is not possible to move the carriage 42 to the coupling position, even when operating (closing) the switch S1. If the proximity switch S3 is closed, i.e. the distance between the two device units 12, 14 is smaller than the minimum distance, and if the segmented arm is not fully (electrically) coupled yet, the carriage 42 moves to the coupling position even without operating the switch S1. If the segmented arm is mechanically and electrically coupled, the switch S2 is closed and the carriage 42 automatically returns to the resting position due to the spring preload.

In the mechanically and electrically coupled state and hence in the operational state, the carriage can be extended by operating (closing) the switch S1 or by operating (opening) the switch S2; hence, the segmented arm 14 may get released or, by letting go the respective switch, the segmented arm 14 can again be tensioned and locked by means of the spring preload.

For decoupling, S1 can be operated (closed) or S2 can be operated (opened) in order to bring the carriage 42 into the coupling position. If the segmented arm 14 is detached from the technical block 12, the electrical contact between the segmented arm 14 and the technical block 12 is first detached, being equivalent to a permanent operation (opening) of the switch S2. After the separation of the electrical contacts, touching of S1 or S2 can be canceled and the carriage 46 remains in the coupling position as long as the proximity switch S3 is (still) closed. If the distance between the magnet 64 and the proximity switch S3 becomes too large, the proximity switch S3 opens and the carriage 46 automatically returns to the resting position due to the spring preload.

Thus, the present invention describes an electrical switching concept on a two-piece surgical device which is operated by force and electrically controlled, while the switching logic is minimizing the risks of the device, which exist in particular prior to or during the adaptation of the second device part.

This means that the assembly and disassembly operation is very safe, on the one hand, as the carriage 42 is able to extend only if it is sufficiently covered by the rear or proximal end of the segmented arm 14, so that it does not represent a source of danger any more. On the other hand, the procedures are very comfortable, as for assembling the two parts the operation of an actuation element is not required on the part of the user, while for disassembly the user has to activate one actuation element only for a short time.

Due to the fact that the switching logic in conjunction with the proximity switch automatically ensures the corresponding movements, it is excluded that the user disregards or forgets this safety means.

However, the present invention is not limited to the embodiments which have been described in detail above, but can be varied within the protection scope of the attached claims. Some of such variation possibilities are set forth in the following.

In the present exemplary embodiment, the technical block as mentioned above is supplied with energy from a further unit (wall plug transformer). As an alternative, the technical block itself may contain or provide all energies. Furthermore, the electronic control system is displaced due to sterilization problems (high temperature, water vapor). With a corresponding adaptation, it could also be accommodated in the technical unit.

In further exemplary embodiments, the switching logic may be slightly modified by the installation of several actuation switches. In the described exemplary embodiment having two actuation elements, however, at least three switches are required. The principle of this safety circuit can be applied to multi-piece devices as well.

The selection of the sensor S3 also results in different exemplary embodiments. Apart from the magnetic proximity switch mentioned above, exemplary embodiments are conceivable in the form of optical sensors, capacitive sensors, inductive sensors, mechanical switching elements, contact points which are bridged by the holding arm, electromagnetic proximity switches, or switching elements which are operated by means of a light barrier or ultrasound.

Further, modified exemplary embodiments are conceivable in which one of the actuation elements S1 and S2 is omitted.

The electronic control system may be built up by means of discrete logic gate components, microcomputers or circuits made up of individual transistors and diodes. By means of corresponding additional components or special programs in the microcomputer, it is also possible to implement time constants filtering the bouncing of the mechanical switching elements. Such time constants may also be used for filtering interferences from transmission lines (said interferences could get coupled in by HF surgical equipment, for instance).

It is likewise possible to eliminate the effects of a "jitter" of the signal coming from the magnet sensor by means of the implementation of time constants. Such a jitter may occur in particular every time if the magnet is moved at a distance from the sensor which is close to the switching threshold. The implementation of time constants further allows to maintain switching states for a minimum or maximum duration.

The invention claimed is:

1. A medical device comprising two device units that can be mechanically coupled to each other,
    the two device units comprising two functional units that can be mechanically coupled to each other in order to be able to actuate the second functional unit by virtue of the first functional unit in a mechanically coupled state;
    the first functional unit can be controlled electrically or electronically and has a mechanical coupling segment which can be brought into a coupling position in order to couple with a corresponding mechanical coupling segment of the second functional unit,
    the medical device further comprising a detection system on at least one device unit for detecting a relative position of the two device units with respect to each other, or a distance of the two device units from each other; wherein
    electrical or electronic control of the first functional unit is configured in such a way that the mechanical coupling segment of the first functional unit can be brought into the coupling position only if the two device units are in a certain relative position with respect to each other or fall below a predetermined minimum distance from each other.

2. The medical device according to claim 1, wherein the detector is a proximity switch or proximity sensor provided on or at least near the coupling segment of the first functional unit, said switch or proximity sensor being able to be triggered by appliances which are provided on or at least near the coupling segment of the second functional unit, said triggering being effected if the first coupling segment is brought near the second coupling segment while falling below the predetermined minimum distance.

3. The medical device according to claim 2, wherein the proximity switch or proximity sensor is installed in the device unit of the first functional unit so as to be flush-mounted or concealed.

4. The medical device according to claim 1, wherein the device units are also electrically coupled if they are mechanically coupled to each other, wherein:
    during coupling of the two device units, an electrical coupling is not effected until a mechanical coupling is completed; and
    during decoupling of the two device units, the electrical coupling is released before the mechanical coupling.

5. The medical device according to claim 4, wherein the coupling segment of the first functional unit is automatically shifted from the coupling position to the predetermined position after the electrical coupling of the two device units.

6. The medical device according to claim 1, wherein the predetermined minimum distance is equal to or smaller than 40 mm.

7. The medical device according to claim 1, wherein the minimum distance is equal to or smaller than 15 mm.

8. A medical device comprising two device units that can be mechanically coupled to each other,
    the two device units comprising two functional units that can be mechanically coupled to each other in order to be able to actuate the second functional unit by virtue of the first functional unit in a mechanically coupled state;
    the first functional unit can be controlled electrically or electronically and has a mechanical coupling segment which can be brought into a coupling position in order to couple with a corresponding mechanical coupling segment of the second functional unit,
    the medical device further comprising a detection system on at least one device unit for detecting a relative position of the two device units with respect to each other, or a distance of the two device units from each other; wherein
    electrical or electronic control of the first functional unit is configured in such a way that the mechanical coupling segment of the first functional unit can be brought into the coupling position only if the two device units are in a certain relative position with respect to each other or fall below a predetermined minimum distance from each other,
    wherein the coupling segment of the first functional unit is spring-biased into a predetermined position and can be brought to the coupling position by external power.

9. The medical device according to claim 8, wherein the coupling segment can be brought into the coupling position by hydraulic or pneumatic pressure.

10. The medical device according to claim 9, wherein the coupling segment of the first functional unit is automatically in the coupling position after the electrical decoupling of the two device units and is kept in the coupling position until the distance between two device units is larger than or equal to the predetermined minimum distance, and is automatically brought into the predetermined position after exceeding the predetermined minimum distance.

11. The medical device according to claim 8, wherein
    in a coupled state of the two device units, the first functional unit and indirectly the second functional unit, can be electrically or electronically actuated by operating a first actuation element provided on the first device unit; and in a decoupled state of the two device units, the coupling segment of the first functional unit is automatically brought into the coupling position by external power, if the two device units are in said certain relative position with respect to each other or have fallen below the predetermined minimum distance with respect to each other.

12. The medical device according to claim 8, wherein in a coupled state of the two device units, the first functional unit and indirectly the second functional unit can be electrically or electronically actuated by operating a second actuation element provided on the second functional unit; and the second actuation element is configured such that the supply of energy for activation of the first functional unit is interrupted during electrical coupling of the two device units.

13. The medical device according to claim 12, wherein the second actuation element is implemented as an electrical break contact, so that the supply of energy for actuation of the first functional unit is interrupted during electrical coupling of the two device units.

14. A method of mechanically coupling two functional units of a two-piece or multi-piece medical device, the medical device having two device units that can be mechanically coupled to each other, the two device units having two functional units that can be mechanically coupled to each other in order to be able to actuate the second functional unit by virtue of the first functional unit in a mechanically coupled state, the first functional unit being controlled electrically or electronically and has a mechanical coupling segment which can be brought into a coupling position in order to couple with a corresponding mechanical coupling segment of the second functional unit, said method comprising the steps of:

detecting a relative position or a distance of the two device units relative to each other; and configuring an electrical or electronic control of the first functional unit in such a manner that the mechanical coupling segment of the first functional unit is brought into the coupling position only if the two device units are in a specific relative position with respect to each other or fall below a predetermined minimum distance with respect to each other.

\* \* \* \* \*